United States Patent
Thomke et al.

(10) Patent No.: US 9,844,425 B2
(45) Date of Patent: Dec. 19, 2017

(54) DENTAL IMPLANT SYSTEM WITH CERAMIC IMPLANT

(71) Applicant: Z-Systems AG, Oensingen (CH)

(72) Inventors: Ernst Thomke, Grenchen (CH); Rubino Di Girolamo, Oberageri (CH); Thomas Hug, Erlenbach (CH); Roger Staudenmann, Busswil b. Buren (CH)

(73) Assignee: Z-SYSTEMS AG, Oensingen (CH)

( * ) Notice: Subject to any disclaimer, the term of this patent is extended or adjusted under 35 U.S.C. 154(b) by 207 days.

(21) Appl. No.: 14/554,603

(22) Filed: Nov. 26, 2014

(65) Prior Publication Data
US 2015/0147724 A1  May 28, 2015

(30) Foreign Application Priority Data

Nov. 27, 2013 (CH) ...................................... 1974/13

(51) Int. Cl.
*A61C 8/00* (2006.01)
(52) U.S. Cl.
CPC .......... *A61C 8/0078* (2013.01); *A61C 8/0012* (2013.01); *A61C 8/0059* (2013.01); *A61C 8/0063* (2013.01); *A61C 8/0065* (2013.01); *A61C 8/0068* (2013.01); *A61C 8/0069* (2013.01); *A61C 8/0074* (2013.01); *A61C 2201/007* (2013.01)

(58) Field of Classification Search
CPC .... A61C 13/001; A61C 13/0003; A61C 13/08
See application file for complete search history.

(56) References Cited

U.S. PATENT DOCUMENTS

| | | | |
|---|---|---|---|
| 2010/0248184 A1* | 9/2010 | Soler ................... | A61C 8/0012 433/172 |
| 2012/0045736 A1* | 2/2012 | Shimko ............... | A61C 8/0006 433/173 |
| 2013/0224689 A1* | 8/2013 | Ishiwata ............. | A61C 8/0066 433/201.1 |
| 2014/0205969 A1* | 7/2014 | Marlin ................ | A61C 8/0001 433/173 |

FOREIGN PATENT DOCUMENTS

| | | |
|---|---|---|
| CH | 707 009 | 3/2014 |
| CH | 707 568 | 8/2014 |
| EP | 2 039 320 | 3/2009 |
| EP | 2 072 020 | 6/2009 |

* cited by examiner

*Primary Examiner* — Jason-Dennis Stewart
(74) *Attorney, Agent, or Firm* — Rankin, Hill & Clark LLP

(57) ABSTRACT

A dental implant system with a ceramic implant and with an abutment, which moreover includes an insert element for the ceramic implant. The insert element is either manufactured from non-ceramic material or is manufactured essentially of injection molded ceramic. The insert element matches with a recess a proximal region of the ceramic implant and is inserted or insertable into the recess. The insert element serves for the fastening of the abutment and for this is equipped with fastening structures. The insert element, which is arranged in the recess of the ceramic implant, is connectable or connected to the ceramic implant by way of a frictional connection and/or positive connection with respect to axial traction.

21 Claims, 9 Drawing Sheets

DENTAL IMPLANT SYSTEM WITH CERAMIC IMPLANT

BACKGROUND OF THE INVENTION

Field of the Invention

The invention is in the field of dental medicine and relates to a dental implant system including a ceramic implant and an abutment.

Description of Related Art

Many of the common dental implant systems are of several parts and include an implant anchored in the bone, and an abutment, on which an attachment element a crown or bridge, for example, is fastened. Multi-part dental implant systems with an implant and an abutment are often called two-part implant systems, irrespective of further components. Two-part dental implant systems are characterised by particularly comprehensive application possibilities in dental prosthetics. Generally, one waits for the implant to be healed in the bone after the implant of a two-part implant system has been anchored in the bone. The abutment is fastened on the implant after the healing-in phase.

Some common dental implant systems are manufactured of ceramic, in particular since ceramic has an extraordinary good biocompatibility and since particularly good aesthetic results are obtained with ceramic implants. Ceramic materials, however, are brittle, which is why ceramic implants are more prone to breakage as compared to implants manufactured from ductile, metallic materials. Two-part ceramic implants are even more prone to breakage in comparison to single-part ceramic implants, but are often preferred on account of the versatile application possibilities. A two-part ceramic implant that displays a particularly breakage-resistant connection between the ceramic implant and the abutment is described, for example, in CH 00460/13.

The more costly manufacturing method of ceramic implant systems is also disadvantageous compared, for example, to implant systems of titanium or titanium alloys. In particular, the machining of ceramic blanks, which is necessary in order to provide ceramic implant parts with the desired inner and outer structures, is time-consuming and costly. Ceramic material, for example, cannot be turned or embossed due to the brittle characteristics. Complicated grinding methods, as are described for example in EP 2,072,020 are usually applied for creating contours on ceramic parts. The manufacture of delicate inner structures with grinding methods is particularly time-consuming. A manufacturing method for inner structures of ceramic implant parts, which in particular is suitable for the creation of insert geometries is described in CH 01744/12.

SUMMARY OF THE INVENTION

It is the object of the invention, to provide a dental implant system with a ceramic implant and an abutment, the dental implant system being improved compared to the state of the art and overcoming disadvantages of known dental implant systems of ceramic material.

The dental implant system according to the invention is a two-part dental implant system with a ceramic implant and an abutment and moreover includes an insert element for the ceramic implant. The insert element is either essentially manufactured of non-ceramic material, which is to say consists completely or essentially of a non-ceramic material, or, alternatively, the insert element is manufactured from injection moulded ceramic and consist of injection moulded ceramic material. The insert element matches with a recess which opens in a proximal region of the ceramic implant and into which the insert element is inserted or is insertable. The proximal opening of the recess is accessible from the proximal side, even if the implant is already implanted into the bone. The insert element serves for fastening the abutment and for this is provided with fastening structures. The insert element inserted in the recess of the ceramic implant, can be or is connected to the ceramic implant by way of a frictional connection and/or positive connection with respect to axial traction (axial pull). The insert element is thus connectable or connected in the recess to the ceramic implant in an adhesive-free manner.

The term dental implant system for this text is defined as a two-part implant system with a ceramic implant and an abutment. The attribute "two-part" thus relates to the presence of a ceramic implant implantable into the bone and of an abutment which can be fastened on the ceramic implant. The dental implant system additionally to these two parts includes the insert element and can moreover include yet further parts. The abutment in the connected condition of the two-part dental implant system is indirectly fastened on the ceramic implant by way of the abutment being fastened on the insert element, and the insert element being fastened on the ceramic implant. The ceramic implant of the two-part implant system is anchored in the bone. Gingival tissue essentially grows around the abutment after its fastening on the implant. Generally, an attachment element such as a crown or a bridge, for example, is fastened on the abutment.

The ceramic implant is manufactured essentially of a ceramic material. The ceramic implant in some embodiments consists exclusively of ceramic material. Therefore, the term ceramic implant is generally used in this text, and the ceramic implant in this text can also be simply termed in an abbreviated manner as an implant. The recess in the proximal region of the ceramic implant is designed as a pocket hole with an opening in the proximal face side of the ceramic implant. The insert element is insertable into this recess or is inserted in the recess. The axial region of the recess, in which the inserted insert element is arranged, is indicated as the insert section of the recess.

The abutment can consist of ceramic material or also include other materials or also be manufactured from non-ceramic materials.

The insert element is either manufactured from a material which in contrast to brittle ceramic material is easy to process or machine, such as a material of the material class of metals or metal alloys such as steel, titanium alloys, or for example of plastics, in particular high performance plastics such as PEEK (polyether ether ketone), PPSU (polyphenylsulfone) or other bio-medical, high-performance polymers. The insert element in some embodiments includes an elastic material, for example a shape memory material such as nitinol.

Or the insert element is manufactured of injection moulded ceramic. It can consist of injection moulded ceramic or include injection moulded ceramic and other material. Injection moulded ceramic unifies the known advantages of ceramic material concerning bio-compatibility and aesthetics and the additional advantage of a more simple manufacturability of delicate structures with the injection moulding method. A ceramic implant with a bonded insert element, which can be manufactured from injection moulded ceramic, is described in the state of the art in EP 2 039 320.

The insert element is shaped in a manner such that it can be inserted into the recess of the ceramic implant and in the inserted condition is sunk completely or at least partly in the recesses. In embodiments with an only partial sinking, the insert element comprises a proximal region that projects beyond the proximal end face of the ceramic implant, whereas a distal region of the insert element is sunk in the recess of the ceramic implant.

The axial positioning of an axial section, region or a structure or likewise in this application is characterised by the terms distal and proximal with respect to the implantation direction, such that the distal direction corresponds to the direction to the apical end of the dental implant (or of a tooth) and the proximal direction corresponds to the coronal direction of the dental implant (or of the a tooth).

With embodiments, in which the insert element is completely sunk in the recess, the insert element does not project beyond the end face of the ceramic implant, but at the most is flush with this or is arranged in an insert section of the recess which is distanced to the axial height of the end face of the ceramic implant in the distal direction. The recess of the ceramic implant in the latter embodiments includes a proximal section of the recess between the axial height of the proximal end face and the insert section.

In some of these and other embodiments, the recess of the ceramic implant comprises a distal end section additionally and distally to the insert section.

The recess forms a cavity with a surface that is arranged in the inside of the ceramic implant. The cavity can be rotationally symmetrical over the whole axial region, and, for example, be designed as a cylindrical or conical cavity, or it can be designed differently in different axial regions of the recess. In some embodiments of the ceramic implant, a section of the recess, for example, is a cylindrical cavity and another section is a conical cavity. The surface of the recess in some embodiments, in one or more sections can be provided with structures such as prominences, deepenings (hollows) and likewise, for example for a positive fit with the abutment and/or with the insert element. The proximal section can be provided with special structures which, for example, cooperate with a distal region of the abutment or which can serve as insert geometry, for example for an insert tool for the implantation of the ceramic implant into the bone, and/or as a rotation lock for the abutment.

The proximal section of the recess widens conically in the proximal direction with some exemplary embodiments of the ceramic implant. In some embodiments of the ceramic implant, the cross-sectional areas of the recess of the proximal section and of the insert section differ, for example with respect to the area content and/or with regard to the outer contours of the cross-sectional areas (cross sections). In some embodiments, for example, the cross-sectional area is circular in the insert section, whereas the cross-sectional area is not circular in the proximal section, but for example is a polygon, in particular a regular polygon, or, for example, a lobed constant-diameter shape of a regular or irregular polygon. In further embodiments the cross-sectional area is circular in the proximal section as well as in the insert section, for example with different circle diameters.

In some embodiments of the dental implant system with a proximal section of the recess of the ceramic implant, this section is designed as an inner cone widening in the proximal direction. In some embodiments, the inner cone in the proximal section of the recess is matched to an outer cone in a distal region of the abutment in such a precisely matching manner, that this distal region is connected in the proximal section of the recess to the ceramic implant with a friction fit (non-positively) in the manner of a morse taper, by way of rotating-in the abutment. Such a friction/non-positive connection of the abutment to the ceramic implant advantageously has the effect that forces acting upon the abutment are transmitted onto the ceramic implant in a manner distributed over a comparatively large contact surface. This reduces the stresses in the connection region of the two-part ceramic implant system which arise due to force effects, and this reduces the proneness to breakage.

The dental implant system in the connected condition is characterised by a connection of the insert element to the ceramic implant, in the recess of the ceramic implant, the connection being frictional (non-positive) and/or positive with respect to axial traction.

At least a part of the outer surface of the insert element is frictionally, also described as non-positively connected to at least a part of the surface of the insert section of the recess, in the connection which is frictional with respect to axial traction. The frictional connection fastens the insert element in the recess as long as a tensile force does not exceed the counterforce between the outer surface of the insert element and the surface of the recess of the ceramic implant, said counterforce being effected by adhesive friction.

In a connection, which is positive with respect to axial traction, the shape of the recess, for example, by way of a structural obstacle such as a projection or a narrowing of the diameter, prevents the insert element inserted into the insert section from being able to be pulled out of the recess. The path in the axial, proximal direction is blocked for the insert element in the positive connection. A connection, which is positive with respect to axial traction thus means that the recess comprises an undercut, by way of which the insert element in the ceramic implant is firmly seated in the recess. The insert element can only be pulled out of the undercut recess of the ceramic implant if the tensile force is so large that it effects a material breakage.

In some embodiments, the dental implant system in the connected condition is connected in the recess to the ceramic implant by way of a frictional fit, in some embodiments by way of a positive fit and on some embodiments by way of a frictional as well as positive fit.

A great advantage of the dental implant system according to the invention is the fact that the insert element can either be manufactured of a material such as metal or plastic or of injection moulded ceramic. Complex and fine structures can be manufactured in a significantly simple technical manner with these materials. The otherwise particularly large time and cost effort for the manufacture of fastening structures for the connection of the ceramic implant and abutment is significantly reduced by way of the use of the insert element according to the invention. The manufacturing costs for the two-part dental implant system according to the invention are thus significantly lower than the manufacturing costs of a conventional, two-part dental implant system of ceramic material.

In contrast to this, the technical design of the insert section of the recess of the ceramic implant for a frictional as well as a positive connection between the insert element and the ceramic implant is comparatively simple and inexpensive. No complicated inner structures are necessary for this. The insert section for a non-positive fit can be designed, for example, as a cylinder without additional surface structures and be manufactured with a conventional cylindrical grinding pencil. The insert section can be undercut and, for example, be designed as an undercut cylindrical insert section or, for example, as a conical insert section widening in the distal direction and be manufactured with an angled cylindrical or a conical grinding disc, for a positive fit, wherein a simultaneous non-positive fit with the insert element is envisaged or not envisaged. Of course, other common surface structures such as ribs and grooves and likewise can also be created for a positive fit.

A further big advantage of embodiments with a frictional fit is the fact that the insert element is connected to the ceramic implant in a particularly firm manner by way of the frictional fit. A typical contact adhesive (e.g.: loctite) has a shear force parallel to the surface of approx. 10 N/mm². A cylindrical sleeve with a radius of 1 mm and a height of 2 mm and which is bonded with loctite tears at a shear force of approx. 62.3 N, whereas the pull-out force of an equally large, screwed-in, expandable insert element lies above 500 N and it is probably the case that the screw breaks before the insert element can be pulled out of the recess.

A further advantage of the two-part ceramic implant system according to the invention is the fact that the connections of the abutment to the insert element and of the insert element to the ceramic implant are free of adhesive. The use of adhesive in two-part implant systems entails various disadvantages, and not only the limited bonding, but also in particular the problem of the adhesive bonding diminishing over time, and meeting the regulatory approval conditions for an additional material are disadvantages that the dental implant system according to the invention overcomes.

A further advantage is the fact that the insert element, in the case of it not consisting of ceramic material but of a metallic material, is completely surrounded by ceramic material in the connected condition of the implant system and is completely shielded or can be shielded from the body tissue. This is due to the fact that in embodiments, in which the insert element is completely sunk in the implant in the connected condition of the dental implant system, the body tissue is only exposed with respect to the ceramic outer side of the ceramic implant. The dental implant system thus retains the excellent characteristics of ceramic implant systems with regard to biocompatibility and aesthetics. Even with embodiments, in which the insert element is not completely surrounded by the ceramic implant and, for example, projects beyond the proximal end face of the ceramic implant, the abutment accordingly can be selected without further ado such that the protruding part of the insert element is covered by the abutment.

In some embodiments of the dental implant system, the insert element is sleeve-like and additionally to an outer surface of the insert element comprises an inner surface of the insert element. The inner surface of the sleeve is provided with a thread or with other structures for fastening the abutment on the insert element, with some sleeve-like insert elements.

The frictional fit between the insert element and the ceramic implant can arise due to the insert element being expandable respectively spreadable, with some exemplary embodiments of the dental implant system. In these embodiments, the insert element is manufactured of a non-ceramic material. The expandable insert element is firstly inserted into the recess of the ceramic implant in the non-expanded which is to say in the pressed-together condition, whereupon the insert element expands due to the absence of the force pressing it together. In some embodiments, the insert element is expanded in the recess by way of external action. The friction fit between at least a part of the outer wall of the insert element and at least a part of the surface of the recess of the ceramic implant arises on account of the expansion.

The insert element is designed as an expansion plug, for example of plastic, in some exemplary embodiments with an expandable insert element. The insert element in further exemplary embodiments is designed as an annular spring or is provided with an annular spring. In further exemplary embodiments, the insert element is designed as a sleeve, which is slotted once or several times and which, for example, is expanded by way of the insertion of a distal region of the abutment, or of a screw or of a pin or likewise. Some of these expandable, sleeve-like embodiments are provided, for example, with an inner thread or with other inner structures.

The insert element is expandable, sleeve-like and provided with an inner thread in some embodiments of the dental implant system. Thus, the abutment can be fastened on the insert element with an abutment screw or with an outer thread, in the distal region of the abutment. In some of these and further embodiments of the dental implant system, the frictional connection of the insert element is created by way of a widening or expansion of the insert element. The expandable insert element is expanded for example by way of a force that is coupled into the abutment or into a tool and is transmitted onto the insert element. A sleeve-like, expandable insert element can be expanded, for example, by way of rotating in the abutment screw.

In some embodiments, the insert element is formed from an elastic or super-elastic material. In some of these embodiments, the elastic or super-elastic material is a shape memory material of a metal alloy, where the insert element is manufactured from shape memory material and can firstly be loosely inserted into the recess of the ceramic implant. The insert element is not expanded and the non-positive connection between the insert element and the ceramic implant does not arise, until after a phase conversion of the shape memory material by way of changing the temperature or by way of applying a mechanical stress. The elastic or super-elastic material is a plastic in some embodiments. The expanding, instead of by way of a force, can also be effected by way of change in temperature in embodiments of an expandable insert element that includes shape memory material.

The insert element in some of these and other embodiments includes a shape memory material that is highly pseudo-elastic (superelastic) in at least one of its conditions, such as nitinol, for example. The expandability of the inert element in such embodiments of an expandable insert element is ensured by one condition of the shape memory material, and no condition change is needed, in order to expand (spread) such an insert element. In such exemplary embodiments, the insert element is inserted into the recess of the ceramic implant, in a tensioned condition, for example in a condition pressed together by pliers, whereupon the insert element expands on letting go of the pliers and creates the non-positive fit with the surface in the insert section of the recess.

In some embodiments of the dental implant system, the insert element is not expandable and is manufactured, for example, of injection moulded ceramic and has a frictional connection between the insert element and the ceramic implant. The insert element of injection mould ceramic has brittle, non-elastic material characteristics and cannot be expanded. In contrast, an adequate adhesive friction between the outer surface of the insert element and the surface of the recess in the insert section can be achieved, for example, by way of axial or radial wedging. In some exemplary embodiments, at least part-regions of the surfaces of the insert element and recess are shaped such that they radially wedge in these regions by way of rotating the insert element relative to the ceramic implant. In some exemplary embodiments, the outer surface of the insert element and the surface of the recess in the insert section are axially wedged, for example by way of two conical clamping surfaces.

In some embodiments of the dental implant system with a non-expandable insert element, the recess of the ceramic implant in the insert section comprises an inner cone, which in a clamping region is matched to an outer cone of the insert element in an precisely fitting manner such that the insert element in the insert section of the recess is frictionally connected to the dental implant by way of a clamping connection. The cone angle of the inner and outer cone are in a range of 3° to 10° or 5° to 8° in some of these embodiments.

In some embodiments, and in particular in embodiments with an insert element of injection moulded ceramic, the insert element is frictionally or positively connected to the ceramic implant in the recess by way of a spring element. In some of these and other embodiments, the spring element as an additional means supports a frictional or positive connection between the insert element and the implant. The spring element can be designed as an annular spring, and fasten the insert element in the recess, for example by way of the spring element being able to be fastened proximally to the insert element in the recess, and the inserted insert element being positively fastened in the insert section by way of this. In some embodiments of the connected dental implant system, the spring elements effects a clamping effect, with which the insert element is non-positively connectable or connected in the insert section to the implant, wherein the spring element is a separate part or is a part that is connected or connectable to the insert element.

The insert element, which is connectable or connected in the recess of the ceramic implant in a frictional manner, serves for fastening the abutment on the insert element, by which means a fastening of the abutment on the ceramic implant is also indirectly effected. The insert element therefore includes fastening structures for fastening the abutment. The term fastening structures in this text indicates at least one fastening structure for the fastening of the abutment on the insert element.

Fastening structures for the fastening of an abutment on an implant of a two-part implant system are known from the state of the art. They are designed, for example, as inner and outer structures that are matched to one another, for example, as an inner and outer thread. Many two-part implants in the state of the art, for example, include an abutment with an outer structure such as an outer thread and an implant with an inner structure such as an inner thread or, for example, an abutment that is fastened with an abutment screw in an inner thread in the proximal region of the implant. Such fastening structures known from the state of the art, for fastening the abutment on an implant can also be applied for fastening the abutment on the insert element and in particular also on the insert element of the dental implant system according to the invention, which is inserted into the recess of the ceramic implant and is connected frictionally to the implant. Apart from the already mentioned threads, for example ribs, pin-like raisings, prominences of all types can serve as outer structures, and grooves, holes and deepenings/hollows of all types can serve as cooperating inner structures. Thus, an abutment, for example, can be fastened on the insert element with a bayonet closure.

In particular, the inner surface is provided with the fastening structures such as the mentioned inner thread, deepenings and/or prominences of all types, such as grooves, ribs, pins, holes etc., in some embodiments, in which the insert element is sleeve-like and also includes an inner surface additionally to the outer surface.

In some embodiments, the abutment is provided with an inner structure, and the insert element is provided with an outer structure that cooperates with this inner structure and is for fastening the abutment on the insert element, wherein in such an embodiment the outer contour of the insert element can be designed projecting beyond the proximal end face of the ceramic implant.

The frictional connection of the insert element to the ceramic implant can be created before the implantation or after the implantation of the ceramic implant into the bone.

In some embodiments of the dental implant system, the insert element is inserted in the recess in the proximal region of the ceramic implant even before the implantation, for example, on the part of the manufacturer.

In other embodiments, the insert element is present as a separate part of the ceramic implant before implantation and not until in situ is it inserted into the ceramic implant and connected to this with a frictional fit.

In some embodiments, the insert element before implantation, for example, on the part of the manufacture or by way of the dental surgeon, is inserted into the ceramic implant, but not until in situ is it frictionally connected in the recess to the ceramic implant.

In some embodiments of the dental implant system, in which the insert element is connected in the recess of the ceramic implant with a positive connection or a positive and frictional connection, with respect to axial traction, the positive fit, for example, is ensured by way of an undercut recess of the ceramic implant. In such embodiments, for example, the insert section of the recesses can be formed cylindrically, wherein the diameter of the cylinder is not the same over the whole region of the insert section, but is greater in a part-section of the insert section, which is arranged distally, than in a part-section of the insert section, which is arranged proximally thereto. In some embodiments with an undercut and with a cylindrical insert section of the recess, the diameter of the cylinder is constant over the whole insert section of the recess and the diameter reduces in size directly proximally adjacent to the insert section. In further exemplary embodiments with an undercut, this is formed by an insert section of the recess, which widens conically in the distal direction, or by at least one part-section of the insert section, which widens conically in the distal direction.

Some of these embodiments of the dental implant, which have a frictional connection as well as a positive connection of the insert element to the ceramic implant, include an insert element that is sleeve-like and expandable. The insert element, for example, is designed as a slotted, sleeve-like hollow cylinder and, pressed together and distally of an undercut it is inserted into the insert section of the recess and let go of. A frictional and positive fit between the insert element and the implant arises on account of the expansion of the insert element and on account of the undercut. In some embodiments, the insert element is designed, for example, as a hollow conical sleeve or the insert element, for example, includes hollow conical sections, where the diameter reduces in the proximal direction of the cone.

In some of these and further embodiments of the dental implant system, in which the insert element with respect to axial traction is connectable or connected to the ceramic implant with a frictional fit, the positive fit is created, for example, by way of inner structures or outer structures on the surface in the insert section of the recess and by way of corresponding outer structures and inner structures respectively of the outer surface of the insert element. Simply manufacturable inner and outer structures can be selected for an as simple as possible manufacturability of the ceramic implant, such as, for example, grooves running in the non-axial direction on the surface of the recess, into which resiliently designed prominences of the insert element fit.

In some embodiments of the dental implant system, the insert element is additionally connected in the recess of the ceramic implant with a positive connection with respect to rotation forces. In some of these embodiments, the recess is provided with an inner structure, for example with an inner geometry and the insert element is provided with a cooperating outer structure, and these structures effect a rotation lock in the connected condition.

In some embodiments of the dental implant system, the abutment and the proximal region of the recess of the ceramic implant includes structures for the rotation lock of the abutment fastened on the ceramic implant. In some of these embodiments, the recess proximally to the insert section includes a proximal region that is shaped in a manner, or provided with special structures, which match with a distal region of the abutment and/or cooperate with this. The proximal region of the recess, for example, can be provided with an inner geometry such as, for example, an inner lobed constant diameter shape or an inner hex (hexagonal socket), which cooperates with an outer geometry arranged in the distal region of the abutment.

A further aspect of the invention relates to a set including a ceramic implant and an insert element for a dental implant system, as is described herein. The ceramic implant includes a recess with a proximal opening, wherein the insert element is insertable or inserted into the recess, and wherein the insert element is manufactured from a non-ceramic material or wherein the insert element is manufactured essentially of injection moulded ceramic and wherein the insert element is provided with structures for a fastening of an abutment on the insert element. The set with a ceramic implant and insert element is characterised in that the insert element, in the recess of the ceramic implant, is connectable or connected to the ceramic implant by way of a connection which is frictional and/or positive with respect to axial traction.

The ceramic implant is packaged with an insert element in a sterile manner in some embodiments of this aspect of the invention, wherein the ceramic implant and the insert element are present as separate parts and wherein the insert element is already inserted into the recess of the ceramic implant.

A further aspect of the invention relates to a set including an abutment and insert element and optionally an abutment screw for a dental implant system, as is described in this text. The set with the abutment and insert element according to this aspect of the invention includes the abutment and optionally an abutment screw, and the set includes the insert element that fits into the recess of the ceramic implant of the dental implant, wherein the insert element is manufactured of non-ceramic material or wherein the insert element is manufactured essentially from injection moulded ceramic and wherein the insert element is provided with structures for a fastening of the abutment on the insert element. The insert element is connectable or connected in the recess of the ceramic implant to the ceramic implant by way of a connection that is frictional and/or positive with respect to axial traction.

Some embodiment examples of the dental implant system are hereinafter illustrated with figures. The invention is not restricted to the combination of features of the invention which are represented in the figures. The figures are not necessarily true to scale. The same reference numerals indicate the same or analogous elements.

BRIEF DESCRIPTION OF THE DRAWINGS

FIG. 4*a*-4*c* in each case show a view (FIG. 4*a*) or perspective view (FIGS. 4*a*, 4*b* and 4*c*) as well as at least one section of exemplary, sleeve-like embodiments of the insert element which are expandable and conically undercut:

DETAILED DESCRIPTION OF THE INVENTION

Figure 1A:
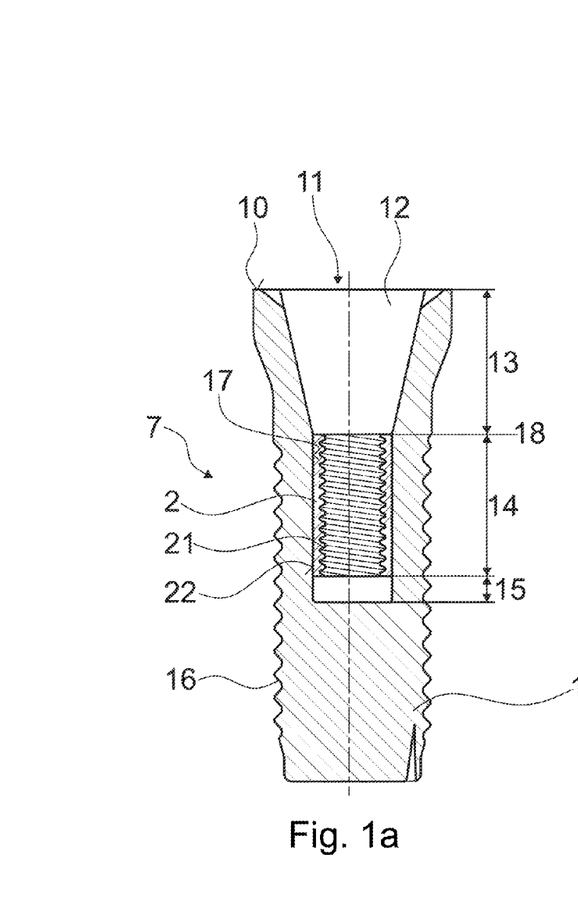
FIG. 1*a* shows a set with a ceramic implant and with an insert element which is inserted therein.
Figure 1B:
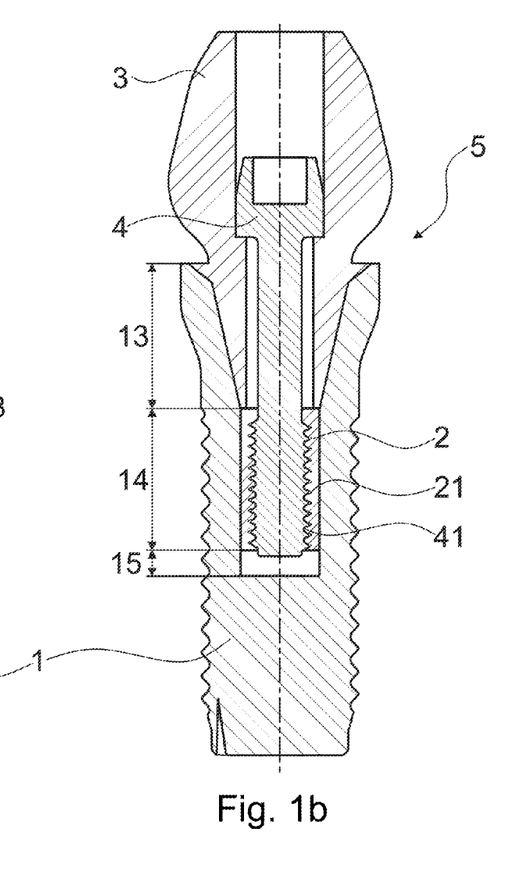
FIG. 1*b* shows the dental implant system in the condition connected to the abutment, fastened in the insert element of the ceramic implant by an abutment screw.

FIGS. 1*a*-1*b* show an exemplary dental implant system 5. A set 7 with a ceramic implant 1, which is essentially implanted into the bone, and with an inserted insert element 2 are shown in FIG. 1*a*. The exemplary dental implant system is shown in the connected condition with the ceramic implant 1, the insert element 2, an abutment 3 and an abutment screw 4 in FIG. 1*b*. The exemplary ceramic implant 1 has a proximal region with a recess 11 with a proximal opening 12. The recess 11 in the axial direction includes three sections: a proximal section 13, an insert section 14 and a distal end section 15. The exemplary ceramic implant 1 includes an outer thread 16.

The proximal section 13 serves for receiving a distal region of the abutment 3 and is formed as a cone widening in the proximal direction. Of course, the proximal section 13 of the recess 11 of the ceramic implant 1 can be differently shaped with a large degree of freedom, for example cylindrically instead of conically or with a cross-sectional area that is not a circle but an oval, a triangle, a rectangle or another regular or irregular polygon, in each case optionally with rounded corners or a lobed constant-diameter shape, and the proximal section 13 can be rotationally symmetrical or not rotationally-symmetrical, but generally the shape of the proximal section 13 of the recess 11 of the ceramic implant 1 is matched to the extent that it can cooperate with the abutment 3. In some embodiments, the proximal section 13 of the recess 11 of the ceramic implant 1 is divided axially also into sub-sections with different cross-sectional areas.

The insert section 14 is arranged distally to the proximal section 13 and serves for receiving the insert element 2. The represented, exemplary insert element 2, which is inserted in the insert section 14, includes an inner thread 21 and is expanded, for example, by an abutment screw 4 with an outer thread 41, by which means a non-positive fit arises between an outer surface 22 of the insert element and an upper surface 17 of the recess 11. The insert section 14 in other embodiments, which are not shown, at least partly can overlap or functionally merge with the proximal section 13, for example, in embodiments in which a distal region of the abutment 3 expands an expandable insert element 2 in the connected condition of the dental implant system 5.

Figure 2:
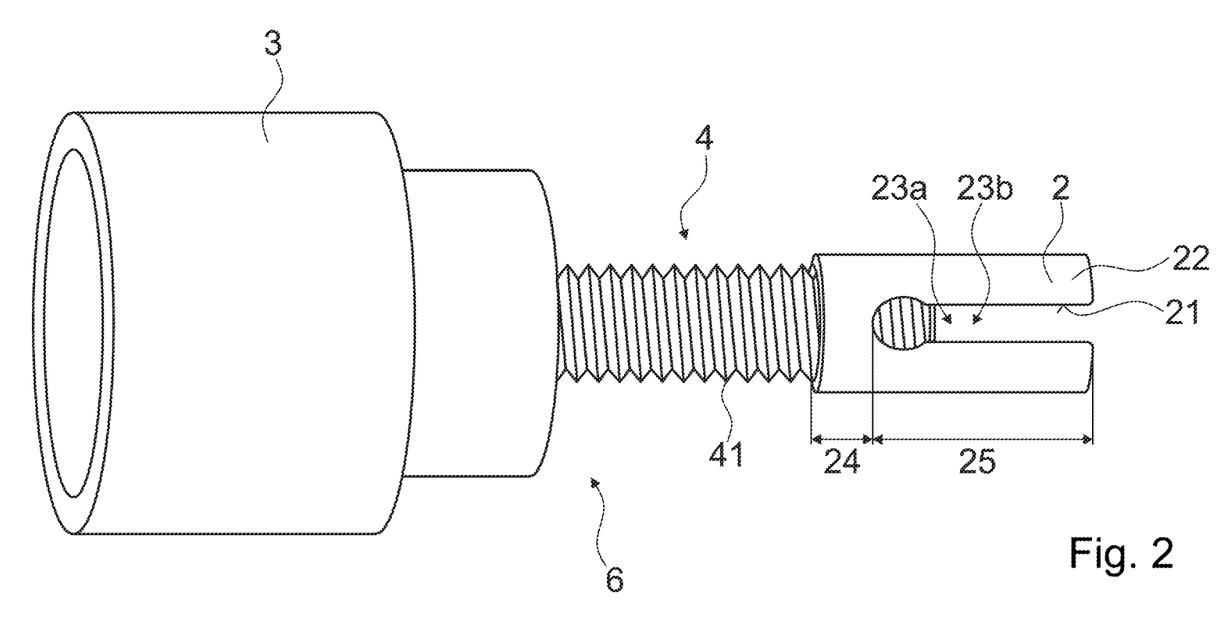
FIG. 2: A schematic view of an exemplary set with an abutment and with an insert element assembled onto an abutment screw.

FIG. 2 shows a view of an exemplary set 6 of a schematically represented abutment 3 with an exemplary, cylindrical, sleeve-like insert element 2, with an inner thread as a fastening structure 21 for an abutment screw 4. In the shown schematic representation, the insert element 2 is preassembled onto an outer thread 41 of the abutment screw 4. The insert element 2 serves for fastening the abutment 3 in a recess 11 of a ceramic implant 1, which is not represented in FIG. 2. The insert element 2 is slotted four times with two visible slots 23*a* and 23*b*, and non-recognisable slots 23*c* and *d*, which are arranged perpendicularly to the slots 23*a* and 23*b* in a distal region 25 of the insert element 2. A proximal region 24 of the insert element 2 is not slotted.

Figure 3A:
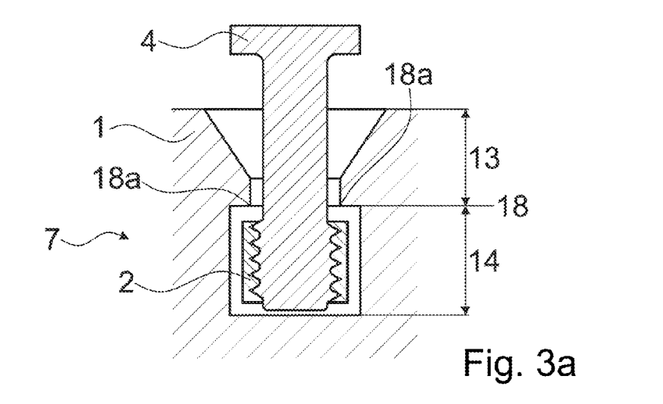
FIG. 3*a*: An example of a cylindrical insert element which is positively connected to the ceramic implant by way of an undercut insert section and which is optionally additionally frictionally connectable to the implant.
Figure 3B:
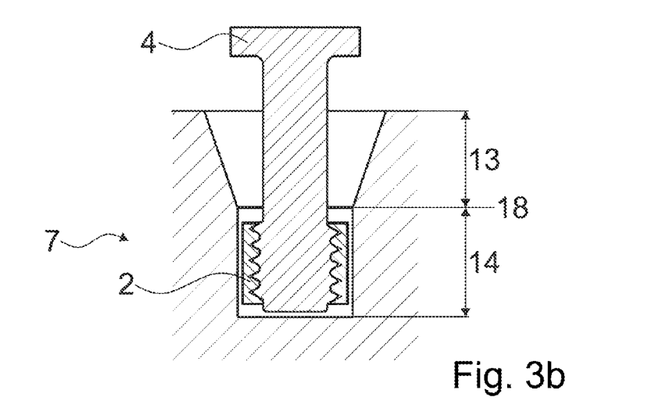
FIG. 3*b*: A cylindrical, expandable insert element of an elastic material such as plastic or metal which is connected purely frictionally to the surface of the recess.
Figure 3C:
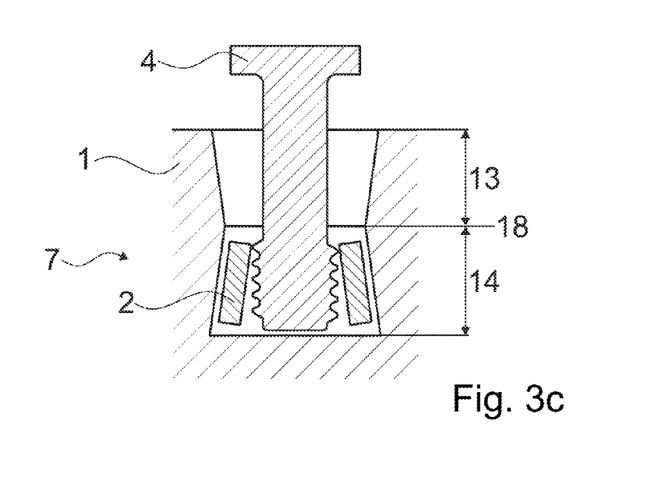
FIG. 3*c*: A conical, expandable insert element which is frictionally as well as positively connected to the surface of the recess of the ceramic implant.

FIGS. 3*a* to 3*c* show schematic representations of exemplary embodiments of a set 7 with a ceramic implant 1 and insert element 2, which is to say of the dental implant system 5 in the connected condition. In particular, exemplary, sleeve-like insert elements 2 inserted into the insert section 14 are in each case represented in a longitudinal section.

FIG. 3*a* shows an example of a cylindrical insert element 2, wherein the insert element 2 is positively connected to the ceramic implant 1 by way of an undercut insert section 14 due to a narrowing of the diameter of the recess 11 at the proximal end 18 of the insert section 14. The narrowing of the diameter of the recess 11 at the proximal end of the insert section 14 forms a projection 18*a* of the surface 17 of the recess 11. This projection 18*a* prevents a withdrawal out of the insert section 14 in the proximal direction of the insert element 2. In some of these exemplary embodiments, the insert element 2 additionally to the positive connection can be frictionally connected to the ceramic implant 1, wherein this is not represented in a recognisable manner in FIG. 3*a*. The insert element 2 is elastic and expands after it has been inserted, in some of these exemplary embodiments, in which the insert element 2 is connected to the ceramic implant 1 with a positive and frictional fit. The insert element 2 in some embodiments is manufactured of a material such as plastic or metal and is slotted in a distal region 25 of the insert element 2 and can be expanded. Some of these and other embodiments of the insert element 2, for example, can be expanded by the abutment screw 4 or a tool or in the case of a shape memory material, by a temperature change or mechanical effect, and thus be frictionally connected to the ceramic implant 1 additionally to the positive fit ensured by the undercut. The insert element is not expandable or extendible in some embodiments of the exemplary cylindrical insert element, in which it consists of injection moulded ceramic.

FIG. 3*b* shows an example of a cylindrical, expandable insert element 2, for example of plastic or metal, which is connectable to the surface of 17 of the recess 11 in the insert section 14 of the ceramic implant 1 in a purely frictional manner. The insert element 2 can, for example, be slotted once or several times and, for example, expand due to an abutment screw 4 being rotated in, or it can include an elastic or superelastic material and be inserted into the insert section 14 in a pressed-together manner and can expand as soon as it is no longer pressed together, and form a friction fit with the implant.

FIG. 3*c* shows an exemplary, conical, expandable insert element 2 of an elastic material such as plastic or metal, in particular of a superelastic shape memory material, which for example, pressed together by way of a pliers, is inserted into the insert section 14 of the recess 11, and a frictional fit between the surface 17 of the recess 11 and the surface 22 of the inset element 2 is formed as soon as it is let go off in the insert region 14. The cone, which widens in the distal direction, forms an undercut insert section 14, which effects an additional positive-fit connection of the insert element 2 to the implant 1. The rotating-in of an abutment screw 4 can effect an extension/expansion of the insert element 2 and retain this even more firmly in the undercut insert section 14.

Figure 4A:
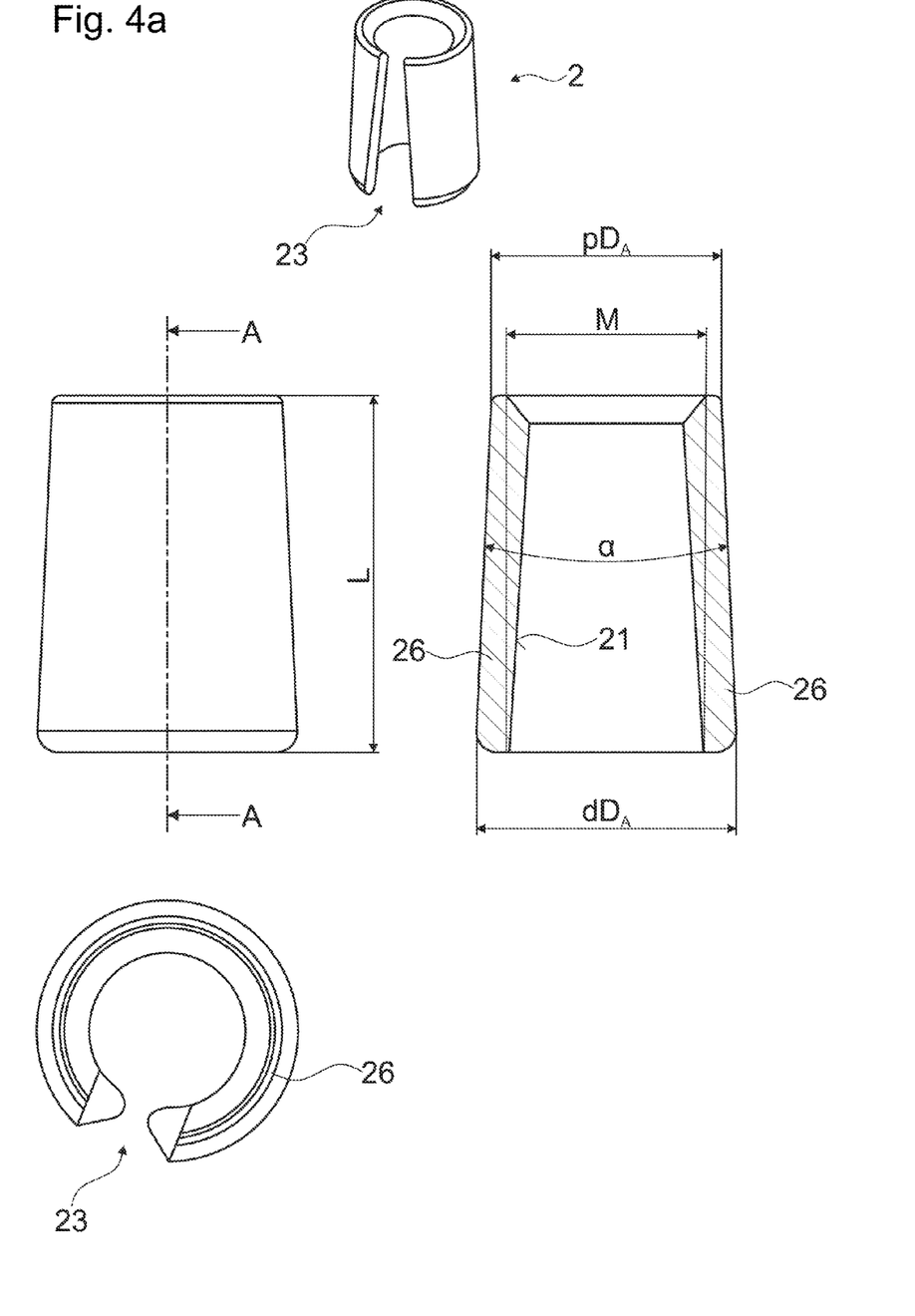
FIG. 4*a*: A conical, sleeve-like insert element slotted once.
Figure 4B:
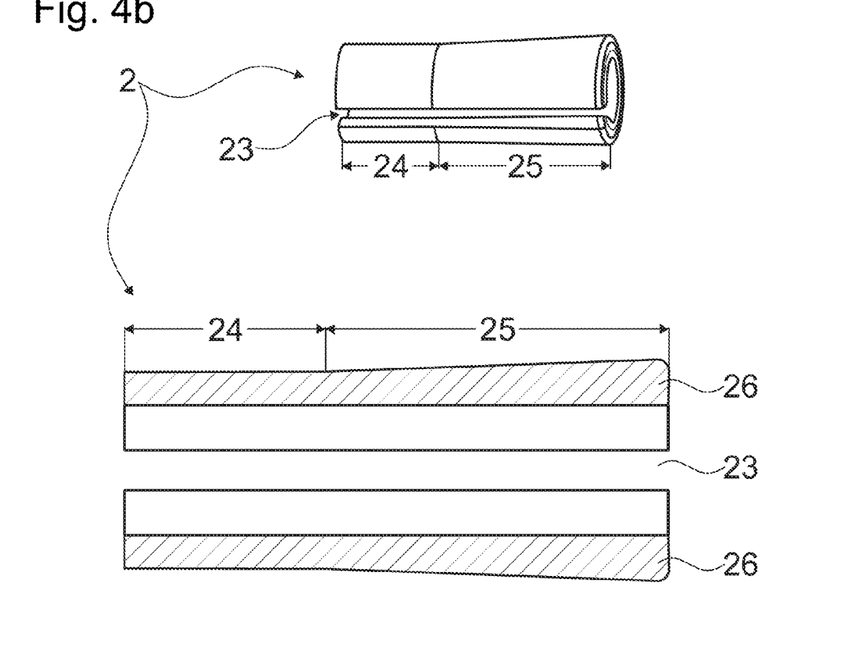
FIG. 4*b*: A conical, sleeve-like insert element slotted once, with a proximally arranged cylindrical section.
Figure 4C:
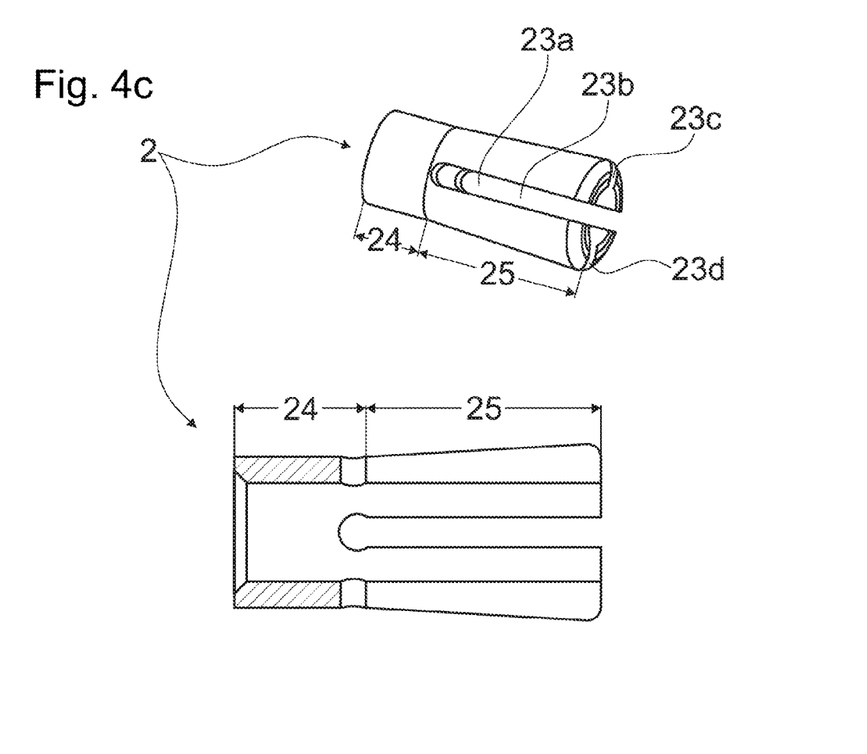
FIG. 4*c*: A fourfold slotted, conical, sleeve-like insert element with a proximally arranged cylindrical section.

FIGS. 4*a*-4*c* show different exemplary embodiments of sleeve-like, slotted, conical insert elements 2 that are expandable or extendable.

FIG. 4*a* shows a conical, sleeve-like insert element 2, which is slotted once, with a slot 23, in a perspective view, a plan view, a longitudinal section and a cross section. The insert element 2 is designed over its whole length L of 1.9 to 2.4 mm, for example, as a hollow cone with a cone angle α of 2° to 20°, for example of 4° to 10° and includes an inner surface 21 and an insert element wall 26. The insert element 2, for example, is manufactured from a shape memory material such as nitinol. The distal outer diameter $dD_A$ of the conical insert element 2, for example, is 1.4 mm to 1.8 mm and, for example, is 0.1 mm to 0.3 mm larger than the proximal outer diameter $pD_A$. The inner surface includes an inner thread 21 such as a metric ISO thread with the dimensions M, for example M1,2.

FIG. 4*b* shows an exemplary embodiment of a sleeve-like insert element 2 that is continuously slotted with a slot 23, in a proximal cylindrical region 24 as well as in a distal conical region 25, represented in a perspective view and in a longitudinal section. Such an expandable insert element 2, for example, is manufactured of an extendible, elastic material of the material class of metal or plastic, in particular of a superplastic shape memory material.

FIG. 4*c* shows a further exemplary embodiment of a sleeve-like, expandable insert element 2, which in a distal conical region 25 is slotted fourfold with 4 slots 23*a*-23*d* and which in a proximal cylindrical region 24 is designed as a peripheral, non-slotted cylinder.

Figure 4D:
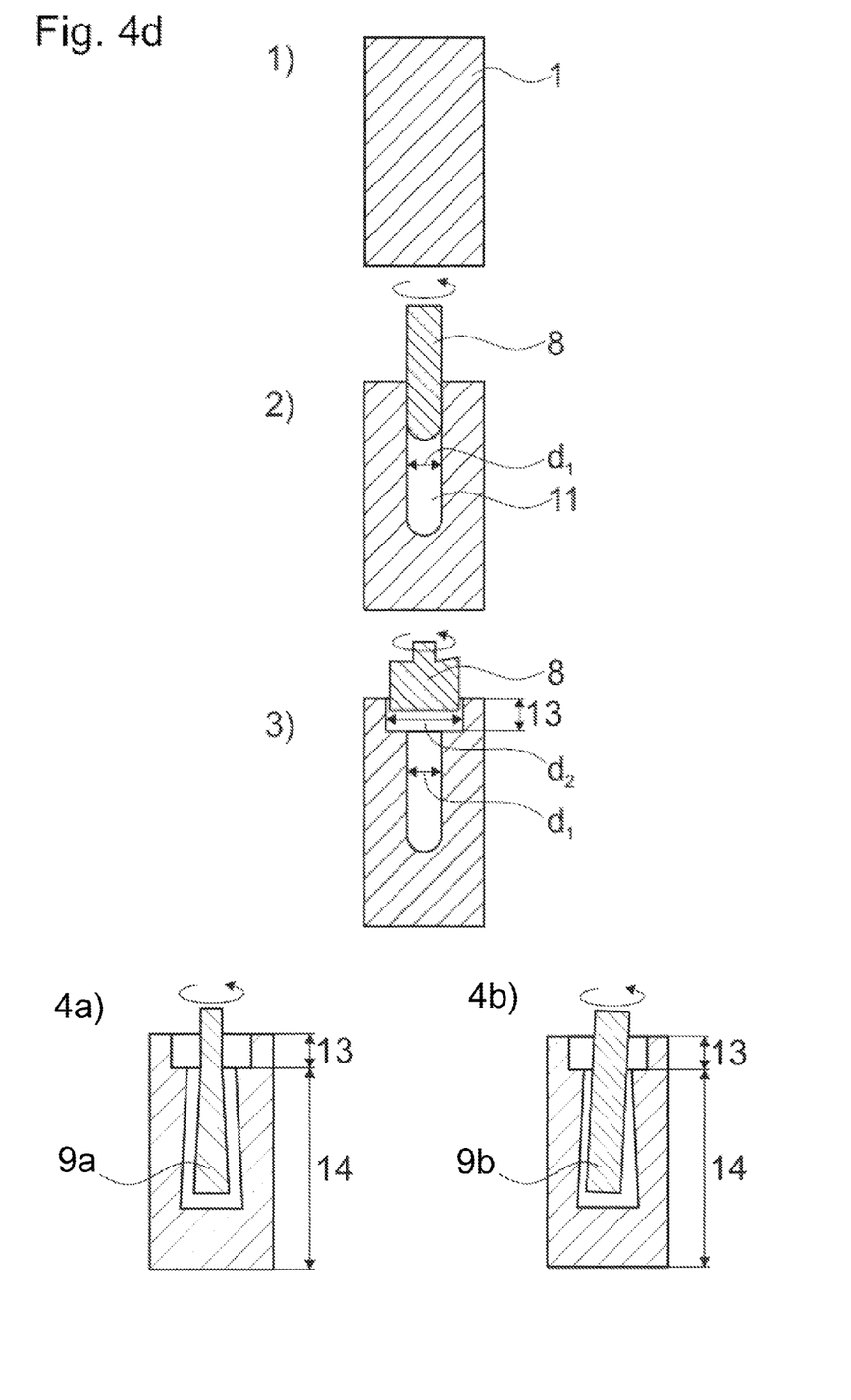
FIG. 4*d*: shows a schematic representation for the manufacture of a conically undercut insert section with a conical grinding disc or alternatively with a cylindrical grinding pencil.

FIG. 4*d* shows a schematic representation with four steps for manufacturing an exemplary embodiment of the ceramic implant 1 with a recess 11 with a widened, cylindrical, proximal section 13 and a conical undercut insert section 14.

In step 1, a blank of a ceramic implant 1 is made available, in which in step 2 a cylindrical recess 11 with a diameter $d_1$ is ground with a hollow, cylindrical grinding pencil 8.

A proximal region 13 with a larger diameter $d_2$ is created with a further cylindrical grinding disk in step 3.

The conical insert section 14, which widens in the distal direction is created in step 4. The conical insert section, for example, is manufactured with an angled, cylindrical grinding pencil or while using a conical grinding pencil 9a, whose diameter widens in the distal direction, as is shown in FIG. 4d, step 4a. Such a conical grinding pencil 9a at the distal end of the conical grinding pencil has a diameter that is smaller than the diameter $d_1$ of the recess 11 created in step 2. For this reason, the conical grinding pencil 9a can be inserted into the recess 11, whose diameter from the distal end of the proximal section 13 has the diameter $d_1$, up to the distal end of the recess. The insert region 14 is ground out as a cone widening in the distal direction by way of a rotation movement of the conical grinding pencil 9a about its own axis and a superimposed further rotation movement along the surface of the recess 11. Alternatively to step 4a, the insert region 14 can be ground out as a cone widening in the distal direction with the help of a cylindrical grinding pencil 9b, in a step 4b. The cylindrical grinding pencil 9b, with a diameter smaller than the diameter $d_1$ of the recess 11 created in step 2, rotates about its own axis and is guided in a tilted manner with respect to an implant axis. A further possible circle-like rotation movement of the cylindrical grinding pencil 9b along the surface of the recess 11 permits the grinding-out of the conically undercut insert section. In further embodiment examples, it is possible to combine the steps 4a and 4b and, for example, to firstly pre-shape the insert region 14 with the tilted, cylindrical grinding pencil 9b, and subsequently to post-machine it with a conical grinding pencil 9a.

Figure 5A:
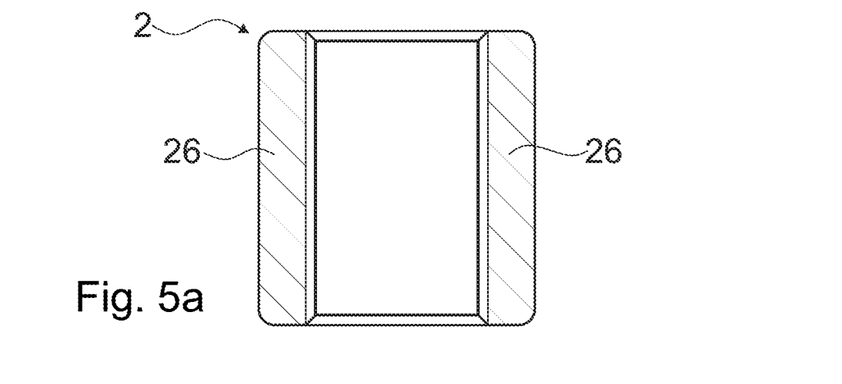
FIG. 5*a*: The insert element which fits into the undercut insert section.
Figure 5B:
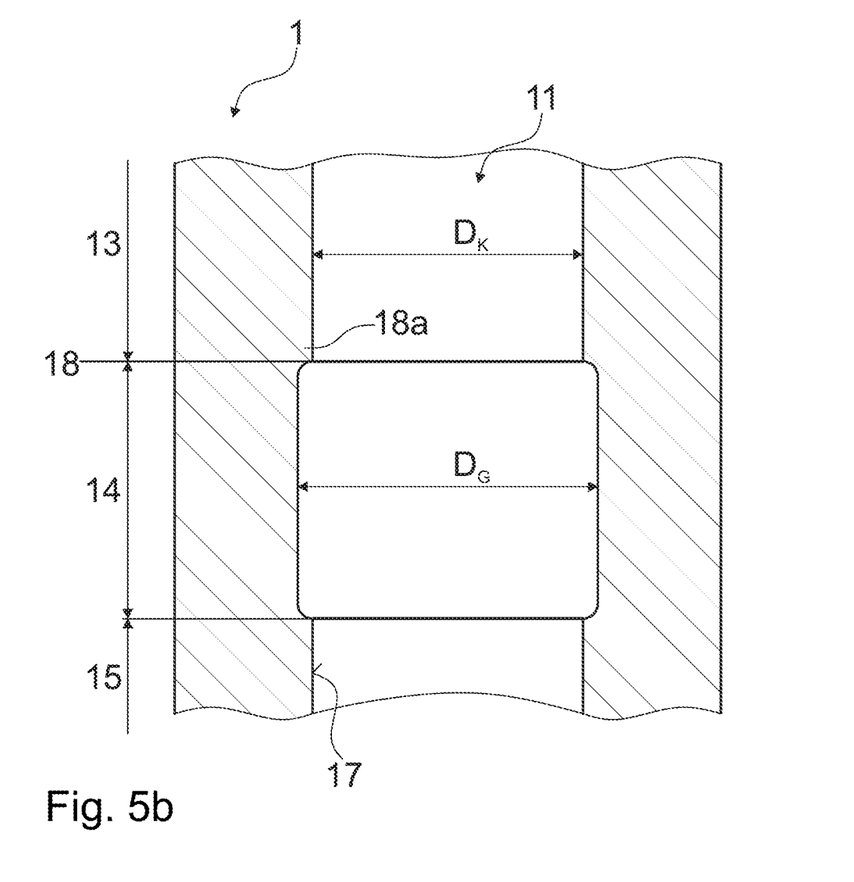
FIG. 5*b*: Cylindrical, undercut insert section of the recess.

FIG. 5 in each case shows a longitudinal section of an exemplary, cylindrical, sleeve-like expandable insert element 2 and of an axial region of an exemplary ceramic implant 1 with an undercut insert section 14 and a proximal section. 13. The insert element 2 forms a positive and optionally an additional non-positive connection to the ceramic implant 1. The exemplary insert element 2, which fits into the undercut insert section 14, is shown in FIG. 5a. The insert element must firstly be pressed together, in order to pass the narrower proximal section 13 of the recess 11 with the smaller diameter $D_K$, so that it can be inserted into the insert section, which is represented in FIG. 5b. This exemplary insert element 2 must therefore be able to be pressed together and expanded again or have elastic characteristics. As soon as the pressed-together insert element 2 is inserted into the undercut insert region 14, it can expand or spread due to the larger diameter $D_G$ in comparison to the smaller diameter $D_K$ in the proximal section 13. A frictional fit between the surface 17 of the recess 11 and the surface 22 of the insert element arises additionally to the positive fit in the case of an adequately large expanding or widening out. The proximal end of the inserted insert element 2 is locked in the recess 11, at the proximal end of the insert region 18 and distally of the projection 18 of the surface 17. It can no longer get past the projection 18a in the expanded or spread condition, and is connected in the insert section 14 to the ceramic implant 1 with a positive fit.

Figure 6:
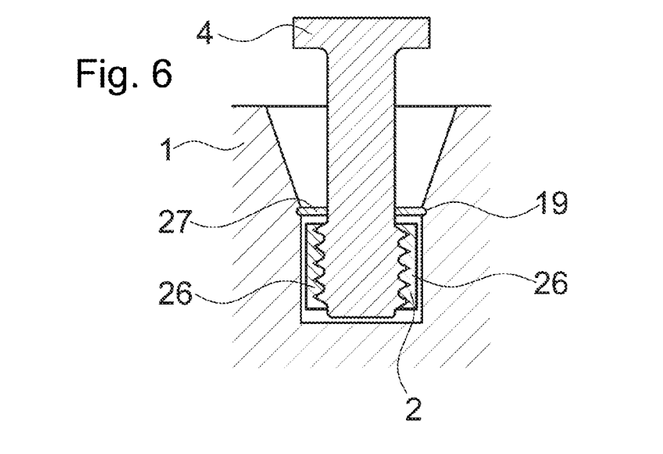
FIG. 6 Schematically shows exemplary embodiments of a non-expandable insert element and of the ceramic implant in a positive connection by way of a spring element introduced proximally to the insert element.

FIG. 6 schematically shows an embodiment example of a positive connection of an exemplary, non-expandable insert element 2, for example of injection moulded ceramic, which is positively connected in the recess 11 of the ceramic implant 1 to the ceramic implant 1 by way of a spring element 27 that is attached proximally of the inserted insert element 2. This is because the spring element 27 effects a narrowing of the diameter of the recess 11 at the proximal end of the insert section 14. The spring element, for example, can be designed as an annular spring. It is manufactured from a shape memory material in some of these and other embodiment examples of the spring element. The insert element in some embodiments, for example, is axially slotted in a sleeve-like manner and the insertion of one or more spring elements effects an expansion of the insert element. With exemplary, non-expandable embodiments of the insert element, for example of injection moulded ceramic, one or more spring elements, for example, of a super-elastic material can be spanned onto the insert element and create a frictional fit with the implant. At least one spring element, for example, can be spanned in at least one optionally peripheral groove on the outer surface of the non-expandable insert element. Thus, the at least one spring element connects the non-expandable spring element in the insert region of the recess with frictional fit.

Figure 7A:
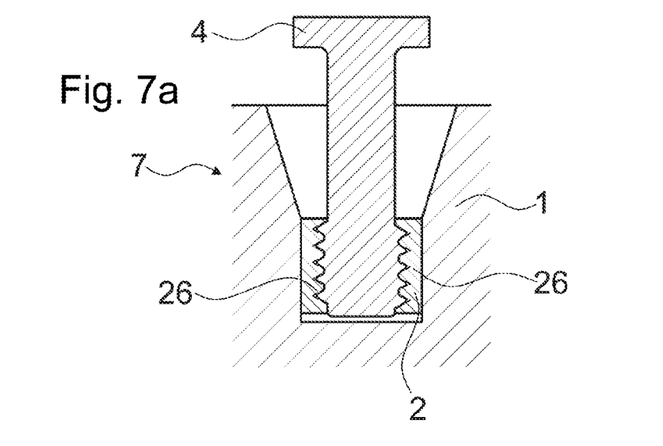
FIG. 7*a*: A longitudinal section through an exemplary set with a ceramic implant and with an inserted insert element.
Figure 7B:
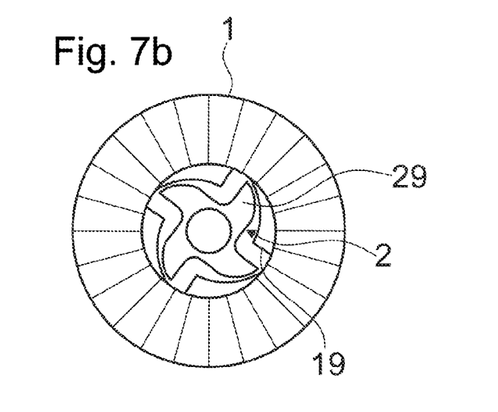
FIG. 7*b*: A view of the set with a ceramic implant and inserted insert element from above.
Figure 7C:
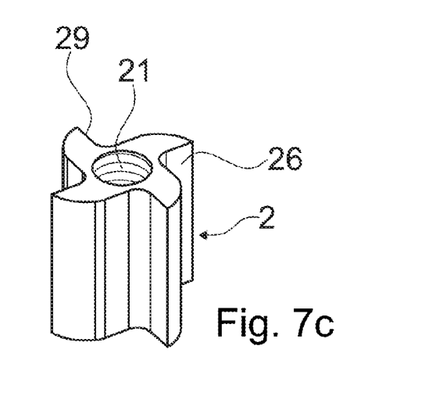
FIG. 7*c*: A perspective view of the insert element.

FIGS. 7a-7c schematically show a further embodiment example of the dental implant system with an exemplary, non-expandable insert element 2, for example of injection moulded ceramic, which is connected to the ceramic implant 1 in the insert section 14 of the recess 11 by way of a frictional connection. The frictional connection arises on rotating the insert element 2 in the recess, by way of the projections 29 of the wall of the insert element 2, which widen in a winged manner, wedging with the wall projections 19 on the surface 17 of the recess of the ceramic implant 1, which widen in the rotation direction, by way of the rotation movement. A friction fit or non-positive fit arises by way of this and firmly clamps the insert element 2 in the insert region 14 and thus connects it to the ceramic implant 1. FIG. 7a shows a section through the ceramic implant 1 with the inserted insert element 2, FIG. 7b a view of the ceramic implant 1 with an inserted insert element 2 from above and FIG. 7c a perspective view of the insert element 2.

In various ones of the embodiments represented in the figures, the insert element 2 is sleeve-like and includes an inner thread 21 for rotating in an abutment screw 4 for fastening an abutment. In some embodiments of the dental implant system 5, which are not represented, the abutment 3 itself includes an outer thread or other connection structures that, in an insert region 14 of the ceramic implant 1, cooperate with fastening structures 21 of the insert element 2 and thus create an indirect connection between the abutment 3 and the implant 1.

These and other of the exemplary embodiments of a set 7 of a ceramic implant 1 and an insert element 2 and which are represented here, or other exemplary embodiments of this which are not represented, can be preassembled and packaged in a sterile manner on the part of the manufacturer, or the set 7 for example on the part of the manufacturer can be packaged in a sterile manner with the insert element 2 and the ceramic implant 1 as separate parts. In the latter case, the insert element 2 and the ceramic implant 1 can be connected to one another before the implantation of the ceramic implant or in situ.

Figure 8A:
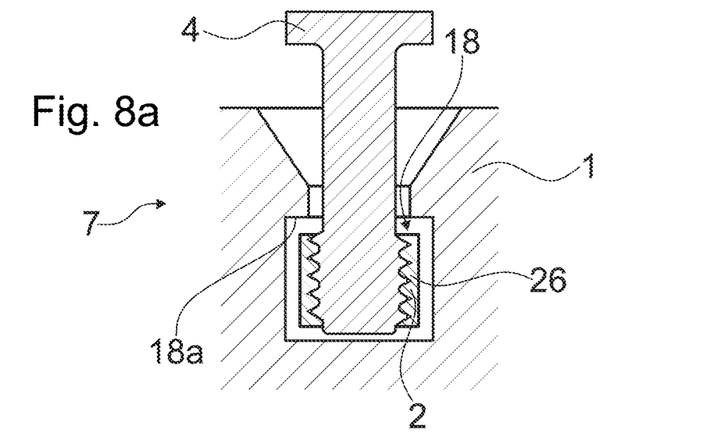
FIG. 8*a*: A longitudinal section through the set with a ceramic implant and inserted insert element.
Figure 8B:
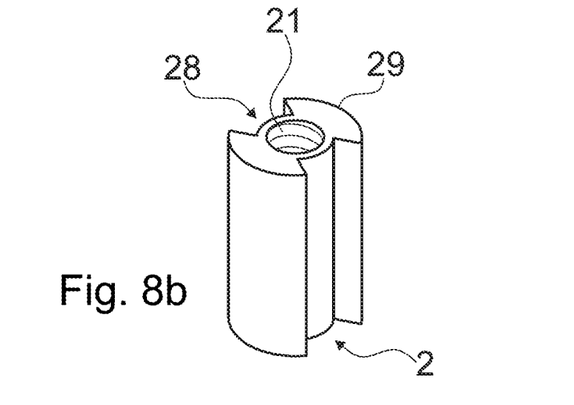
FIG. 8*b*: A perspective view of the insert element.
Figure 8C:
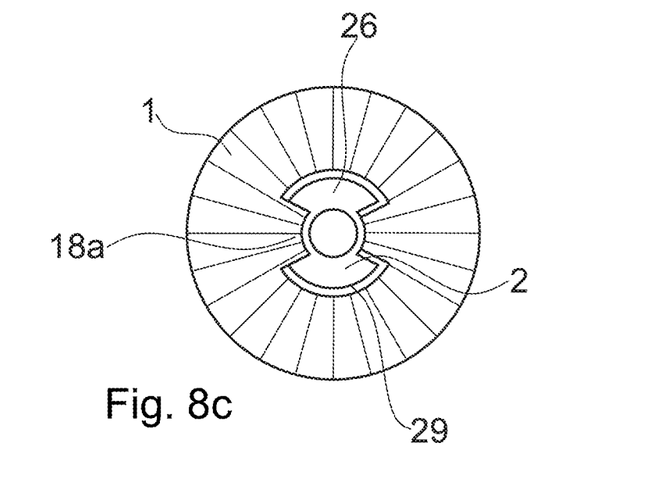
FIG. 8*c*: A view of the set with a ceramic implant with an inserted insert element, from above.

FIGS. 8a-8c schematically show a further embodiment example of the dental implant system 5 or of the set 7 with an exemplary, non-expandable insert element 2, for example of injection moulded ceramic, which is connected to the ceramic implant 1 in the insert section 14 of the recess 11 by way of a positive connection. FIG. 8a shows a cross section through the set 7 with the insert element 2, which is inserted in the implant 1 and which, by way of a projection 18a in the recess 11 at the proximal end 18 of the insert region 14, is locked in the recess 11 in the ceramic implant 1 with a positive fit in the manner of a bayonet closure, as soon as the inserted insert element is pushed below the projection 18a by way of a rotation movement. FIG. 8b shows a perspective view of the sleeve-like insert element 2 with an inner thread as a fastening structure 21 for fastening the abutment 3 and with two cut-outs or hollows 28 in the wall of the insert element 2 and two wall thickenings 29. FIG. 8c shows a view from above, onto the insert element 2 already inserted into the ceramic implant 1, wherein the insert element 2 is only inserted into the insert section 14 of the recess 11, but is not yet rotated, thus is not yet locked with its wall thickenings 29 below the projections 18a in the insert section 14 and is therefore not yet firmly connected to the ceramic implant 1.

LIST OF REFERENCE NUMERALS 1 ceramic implant
10 proximal end face of the ceramic implant
11 recess
12 proximal opening of the recess
13 proximal section of the recess
14 insert section of the recess
15 distal end section of the recess
16 outer thread of the ceramic implant
17 surface of the recess
18 proximal end of the insert section
18a projection of the surface 17 of the recess 11 at the proximal end 18 of the insert section 14
19 surface structure, for example a wing-like wall thickening or a deepening in the surface 17 of the recess, for example in the insert region 14 of the recess 11
2 insert element
21 fastening structure of the insert element
22 outer surface of the insert element
23 slot or slots 23a, 23b, 23c, 23d
24 proximal region of the insert element
25 distal region of the insert element
26 wall of a sleeve-like insert element
27 spring element for fastening the insert element in the insert section
28 wall region of the insert element 2 with an indentation in the wall
29 wall region of the insert element with a prominence or thickening
3 abutment
4 abutment screw
41 outer thread of the abutment screw
5 dental implant system with an insert element and abutment, all in the connected condition
6 set with abutment, abutment screw and insert element in the preassembled condition
7 set with a ceramic implant and insert element in the connected condition
8 cylindrical grinding pencil or cylindrical grinding disc
9 conical grinding pencil

The invention claimed is:
1. A dental implant system, comprising:
a ceramic dental implant,
an abutment, said abutment being equipped to be secured to the implant, and
an insert element; and,
an abutment screw, the abutment screw comprising a fastening thread;
wherein the implant extends between a proximal end and a distal end and defines an opening having a mouth in the proximal end and extending distally therefrom,
wherein the insert element is received in the opening,
wherein the insert element comprises a fastening structure adapted to the fastening thread so that the fastening thread engaging with the fastening structure secures the abutment screw relative to the insert element for fastening of the abutment on the insert element by way of the fastening thread engaging with the fastening structure,
and wherein the insert element is secured to the implant by way of at least one of a frictional connection and a positive-fit connection with respect to axial traction when the insert element is inserted in the opening and when the fastening thread engages with the fastening structure,
whereby the abutment is capable of being secured to the implant by the abutment screw with the fastening thread engaging with the fastening structure when the insert element is inserted in the opening.

2. The dental implant system according to claim 1, wherein the insert element is made of non-ceramic material.

3. The dental implant system according to claim 2, wherein the insert element is expandable and, when expanded, is frictionally secured to the implant.

4. The dental implant system according to claim 1, wherein the insert element is made of injection molded ceramic material.

5. The dental implant system according to claim 1, wherein the insert element, when inserted in the opening and when the fastening thread engages with the fastening structure, is secured to the implant at least by frictional connection with respect to axial traction.

6. The dental implant system according to claim 1, wherein the insert element, when inserted in the opening and when the fastening thread engages with the fastening structure, is secured to the implant at least by positive-fit connection with respect to axial traction.

7. The dental implant system according to claim 1, wherein the insert element is sleeve-like and comprises an inner thread for threadingly receiving an outer thread of the fastening thread.

8. The dental implant system according to claim 7, wherein the insert element expands by the fastening thread engaging with the fastening structure.

9. The dental implant system according to claim 1, further comprising a spring element, wherein the spring element is a separate part or a part connected to the insert element, and wherein the spring element, when the insert element is secured to the implant, is frictionally connected in the opening.

10. The dental implant system according to claim 1, wherein the insert element comprises a shape memory material.

11. The dental implant system according to claim 1, wherein the insert element is equipped to be inserted into the opening before implantation.

12. The dental implant system according to claim 1, wherein the insert element is separate from the implant, and is equipped to be inserted in the opening in situ to the implant after implantation.

13. The dental implant system according to claim 1, wherein the opening is cylindrical at least in an insert section, wherein the diameter of the opening in the insert section or in a part section of the insert section is larger than a diameter of the opening in a proximal section proximally adjacent to the insert section.

14. The dental implant system according to claim 1, wherein the opening in an insert section widens conically in a distal direction, or wherein the opening comprises at least one conical part-section of an insert section, the conical part-section widening in the distal direction.

15. The dental implant system according to claim 1, wherein the insert element is secured in the opening with a positive connection with respect to rotation forces.

16. The dental implant system according to claim 1, wherein the abutment with respect to rotation forces is additionally equipped with a rotation lock between the abutment and a proximal section of the opening.

17. The dental implant system according to claim 1, wherein the insert element comprises an inner opening through which the abutment screw extends when the abutment is fastened on the insert element.

18. The dental implant system according to claim 17, wherein the inner opening is a through opening extending from a proximal end of the insert element to a distal end thereof.

19. The dental implant system according to claim 1, wherein the insert element has an axially running slit.

20. A dental implant set, comprising:
a ceramic dental implant,
an abutment screw, the abutment screw comprising a fastening thread, and
an insert element,
wherein the implant extends between a proximal end and a distal end and defines an opening having a mouth in the proximal end and extending distally therefrom,
wherein the insert element is received in the opening,
wherein the insert element comprises a fastening structure adapted to the fastening thread so that the fastening thread engaging with the fastening structure secures the abutment screw relative to the insert element for fastening of an abutment to the insert element by way of the fastening thread engaging with the fastening structure,
and wherein the insert element is secured to the implant by way of at least one of a frictional connection and a positive-fit connection with respect to axial traction when the insert element is inserted in the opening and when the fastening thread engages with the fastening structure, to secure the abutment to the implant by the abutment screw with the fastening thread engaging with the fastening structure when the insert element is inserted in the opening.

21. A set, comprising:

an abutment, equipped to be secured to an implant, and for an attachment element to be fastened thereto, wherein the implant extends between a proximal end and a distal end and defines an opening having a mouth in the proximal end and extending distally therefrom, an abutment screw, the abutment screw comprising a fastening thread, and an insert element, wherein the insert element is in shaped to match with the opening of the implant, wherein the insert element comprises a fastening structure adapted to the fastening thread so that the fastening thread engaging with the fastening structure secures the abutment screw relative to the insert element for fastening of the abutment on the insert element by way of the fastening thread engaging with the fastening structure, and wherein the insert element is configured to be secured to the implant by way of at least one of a frictional connection and a positive-fit connection with respect to axial traction when the insert element is inserted in the opening of the implant and when the fastening thread engages with the fastening structure, whereby the abutment is capable of being secured to the implant by the abutment screw with the fastening thread engaging with the fastening structure when the insert element is inserted in the opening.

* * * * *